US008940792B2

(12) United States Patent
Myntti

(10) Patent No.: US 8,940,792 B2
(45) Date of Patent: Jan. 27, 2015

(54) ANTIMICROBIAL COMPOSITION AND METHODS FOR USING SAME

(71) Applicant: Microbial Defense Systems, LLC, Jacksonville, FL (US)

(72) Inventor: Matthew Franco Myntti, St. Augustine, FL (US)

(73) Assignee: Next Science, LLC, Jacksonville, FL (US)

( * ) Notice: Subject to any disclaimer, the term of this patent is extended or adjusted under 35 U.S.C. 154(b) by 0 days.

(21) Appl. No.: 13/679,994

(22) Filed: Nov. 16, 2012

(65) Prior Publication Data
US 2013/0079407 A1    Mar. 28, 2013

Related U.S. Application Data

(63) Continuation of application No. 12/573,340, filed on Oct. 5, 2009, now abandoned.

(60) Provisional application No. 61/103,214, filed on Oct. 6, 2008.

(51) Int. Cl.
| | | |
|---|---|---|
| A61K 31/205 | (2006.01) | |
| A61K 31/16 | (2006.01) | |
| A01N 37/18 | (2006.01) | |
| A01N 41/04 | (2006.01) | |
| A01N 25/30 | (2006.01) | |
| A01N 37/36 | (2006.01) | |
| A01N 33/12 | (2006.01) | |

(52) U.S. Cl.
CPC ............... *A01N 41/04* (2013.01); *A01N 25/30* (2013.01); *A01N 37/36* (2013.01); *A01N 33/12* (2013.01)
USPC .......................................... 514/556; 514/642

(58) Field of Classification Search
CPC ....... A01N 25/30; A01N 37/36; A01N 41/04; A01N 33/12; A01N 2300/00
USPC .................................. 514/556, 642
See application file for complete search history.

(56) References Cited

U.S. PATENT DOCUMENTS

| | | |
|---|---|---|
| 3,422,186 A | 1/1969 | Sasmor |
| 4,002,775 A | 1/1977 | Kabara |
| 4,067,997 A | 1/1978 | Kabara |
| 4,107,328 A | 8/1978 | Michaels |
| 4,323,551 A | 4/1982 | Parran, Jr. |
| 4,851,521 A | 7/1989 | della Valle et al. |
| 5,017,229 A | 5/1991 | Burns et al. |
| 5,145,664 A | 9/1992 | Thompson |
| 5,166,331 A | 11/1992 | della Valle et al. |
| 5,208,257 A | 5/1993 | Kabara |
| 5,229,103 A | 7/1993 | Eagle et al. |
| 5,246,964 A | 9/1993 | Ueno |
| 5,290,552 A | 3/1994 | Sierra et al. |
| 5,326,567 A | 7/1994 | Capelli |
| 5,348,678 A | 9/1994 | Hodam, Jr. et al. |
| 5,442,053 A | 8/1995 | della Valle et al. |
| 5,480,658 A | 1/1996 | Melman |
| 5,534,544 A | 7/1996 | Plaut et al. |
| 5,543,383 A | 8/1996 | Parker |
| 5,575,815 A | 11/1996 | Slepian et al. |
| 5,631,241 A | 5/1997 | della Valle et al. |
| 5,644,049 A | 7/1997 | Giusti et al. |
| 5,662,913 A | 9/1997 | Capelli |
| 5,676,964 A | 10/1997 | della Valle et al. |
| 5,709,546 A | 1/1998 | Waggoner |
| 5,763,410 A | 6/1998 | Edwardson et al. |
| 5,895,781 A | 4/1999 | Neumiller et al. |
| 5,910,420 A | 6/1999 | Tuompo et al. |
| 5,925,334 A | 7/1999 | Rubin et al. |
| 6,001,870 A | 12/1999 | Henkel |
| 6,013,657 A | 1/2000 | Lavon et al. |
| 6,063,061 A | 5/2000 | Wallace et al. |
| 6,143,330 A | 11/2000 | Aaltonen et al. |
| 6,149,822 A * | 11/2000 | Fabri et al. ................. 210/764 |
| 6,156,294 A | 12/2000 | Mautone |
| 6,156,792 A | 12/2000 | Hatton et al. |
| 6,203,822 B1 | 3/2001 | Schlesinger et al. |
| 6,224,857 B1 | 5/2001 | Romeo et al. |

(Continued)

FOREIGN PATENT DOCUMENTS

| | | |
|---|---|---|
| EP | 1374856 A1 | 1/2004 |
| FR | 2710529 A1 | 4/1995 |

(Continued)

OTHER PUBLICATIONS

J.O. Anglen et al., "The Efficacy of Various Irrigation Solutions in Removing Slime-Producing *Staphylococcus*," J. Orthop. Trauma, 1994, vol. 8, No. 5, pp. 390-396, (Raven Press, Ltd.; New York, NY).

(Continued)

*Primary Examiner* — Blessing M Fubara
(74) *Attorney, Agent, or Firm* — Zollinger & Burleson Ltd.

(57) ABSTRACT

An aqueous composition adapted to kill bacteria in both planktonic and biofilm states is lethal toward a wide spectrum of gram positive and gram negative bacteria as well as other microbes. The composition, which is slightly to moderately acidic, includes a significant amount of one or more surfactants and large amounts of osmotically active solutes. The composition can be applied directly to a site of bacterial growth. Even when the bacteria is in biofilm form, the surfactant component(s) begin to kill the bacteria before the macromolecular matrix is removed or dislodged from the site.

21 Claims, No Drawings

(56) References Cited

U.S. PATENT DOCUMENTS

| | | |
|---|---|---|
| 6,248,371 B1 | 6/2001 | Domenico |
| 6,284,804 B1 | 9/2001 | Singh et al. |
| 6,342,251 B1 | 1/2002 | Illum et al. |
| 6,375,963 B1 | 4/2002 | Repka et al. |
| 6,395,295 B1 | 5/2002 | Hills et al. |
| 6,395,746 B1 | 5/2002 | Cagle et al. |
| 6,423,333 B1 | 7/2002 | Stedronsky et al. |
| 6,423,694 B1 | 7/2002 | Drutz et al. |
| 6,541,460 B2 | 4/2003 | Petito |
| 6,610,314 B2 | 8/2003 | Koenig et al. |
| 6,616,913 B1 | 9/2003 | Mautone |
| 6,623,513 B2 | 9/2003 | Biel |
| 6,676,930 B2 | 1/2004 | Mautone |
| 6,685,697 B1 | 2/2004 | Arenberg et al. |
| 6,686,346 B2 | 2/2004 | Nilsson et al. |
| 6,701,940 B2 * | 3/2004 | Tsibouklis et al. ......... 134/25.2 |
| 6,706,290 B1 | 3/2004 | Kajander et al. |
| 6,723,709 B1 | 4/2004 | Pressato et al. |
| 6,762,160 B2 | 7/2004 | Barbeau et al. |
| 6,812,196 B2 | 11/2004 | Rees et al. |
| 6,855,678 B2 | 2/2005 | Whiteley |
| 6,867,233 B2 | 3/2005 | Roselle et al. |
| 6,869,938 B1 | 3/2005 | Schwartz et al. |
| 6,891,037 B1 | 5/2005 | Hasler et al. |
| 6,919,348 B2 | 7/2005 | Wei |
| 6,936,579 B2 | 8/2005 | Urban |
| 6,953,772 B2 | 10/2005 | Lopes |
| 6,962,813 B2 | 11/2005 | Pier et al. |
| 6,989,195 B2 | 1/2006 | Anderson |
| 7,090,882 B2 | 8/2006 | Koefod et al. |
| 7,119,217 B2 | 10/2006 | Jiang et al. |
| 7,128,897 B2 | 10/2006 | Osbakken et al. |
| 7,220,431 B2 | 5/2007 | Sawchuk et al. |
| 7,238,363 B2 | 7/2007 | Monsouri et al. |
| 7,244,841 B2 | 7/2007 | Love et al. |
| 7,341,983 B2 | 3/2008 | Pedersen et al. |
| 7,410,480 B2 | 8/2008 | Muni et al. |
| 7,446,089 B2 | 11/2008 | Singh et al. |
| 7,494,963 B2 | 2/2009 | Ahmed et al. |
| 7,544,192 B2 | 6/2009 | Eaton et al. |
| 7,691,829 B2 | 4/2010 | Petito et al. |
| 7,714,011 B2 | 5/2010 | Clarot et al. |
| 7,803,150 B2 | 9/2010 | Chang et al. |
| 7,848,487 B2 | 12/2010 | Miekka et al. |
| 7,959,943 B2 * | 6/2011 | Hissong et al. ............... 424/437 |
| 7,976,873 B2 | 7/2011 | Myntti et al. |
| 7,993,675 B2 | 8/2011 | Oliver et al. |
| 8,784,790 B2 | 7/2014 | Myntti et al. |
| 2001/0051613 A1 | 12/2001 | Illum et al. |
| 2003/0079758 A1 | 5/2003 | Siegel et al. |
| 2003/0133883 A1 | 7/2003 | Finnegan et al. |
| 2003/0139382 A1 | 7/2003 | Wall et al. |
| 2004/0101506 A1 | 5/2004 | Fust |
| 2004/0162230 A1 * | 8/2004 | Jenevein et al. ............... 510/504 |
| 2004/0214753 A1 | 10/2004 | Britten et al. |
| 2005/0003007 A1 | 1/2005 | Boix et al. |
| 2005/0042240 A1 | 2/2005 | Utterberg et al. |
| 2005/0064508 A1 | 3/2005 | Belcher et al. |
| 2005/0080396 A1 | 4/2005 | Rontal |
| 2005/0106728 A1 | 5/2005 | Burgess et al. |
| 2005/0220895 A1 | 10/2005 | Bucalo et al. |
| 2005/0226937 A1 | 10/2005 | O'Hagan et al. |
| 2005/0282722 A1 | 12/2005 | McReynolds et al. |
| 2006/0003008 A1 | 1/2006 | Gibson et al. |
| 2006/0018945 A1 | 1/2006 | Britigan et al. |
| 2006/0045850 A1 | 3/2006 | Namburi et al. |
| 2006/0051385 A1 | 3/2006 | Scholz |
| 2007/0207192 A1 | 9/2007 | Holl et al. |
| 2007/0264296 A1 | 11/2007 | Myntti |
| 2008/0176306 A1 | 7/2008 | MacPhee et al. |
| 2008/0248558 A1 | 10/2008 | Deinhammer et al. |
| 2008/0274932 A1 * | 11/2008 | Smith et al. ................... 510/225 |
| 2009/0005339 A1 | 1/2009 | Scholz et al. |
| 2009/0011097 A1 | 1/2009 | Koefod et al. |
| 2010/0016267 A1 | 1/2010 | Theeuwes et al. |
| 2010/0086576 A1 | 4/2010 | Myntti |
| 2010/0240770 A1 | 9/2010 | Qi et al. |
| 2011/0245757 A1 | 10/2011 | Myntti et al. |
| 2012/0288469 A1 | 11/2012 | Myntti |

FOREIGN PATENT DOCUMENTS

| | | |
|---|---|---|
| JP | 2009-137861 A | 6/2009 |
| WO | 9405330 A1 | 3/1994 |
| WO | 03061579 A2 | 7/2003 |

OTHER PUBLICATIONS

Z. Bendouah et al., "Biofilm formation by *Staphylococcus aureus* and *Pseudomonas aeruginosa* . . . ," Otolaryngology-Head and Neck Surgery, 2006, vol. 134, No. 6, pp. 991-996, (Amer. Acad. of Otolarngology-Head and Neck Surgery Foundation; Alexandria, Virginia).

M.S. Benninger et al., "Adult chronic rhinosinusitis: Definitions, diagnosis, epidemiology, and pathophysiology," Supplement to Otolaryngology-Head and Neck Surgery, 2003, vol. 129, No. 3, pp. S1-S32 (American Academy of Otolaryngology-Head and Neck Surgery Foundation; Alexandria, Virginia).

N. Bhattacharyya, "Clinical outcomes after endoscopic sinus surgery," Current Opinion in Allergy & Clinical Immunology, 2006, 6(3), pp. 161-171 (Lippincott Williams & Wilkins, Inc.; Philadelphia, Pennsylvania)—abstract only.

N. Bhattacharyya et al., "The Microbiology of Recurrent Rhinosinusitis After Endoscopic Sinus Surgery," Arch. Otolaryngol.—Head and Neck Surg., 1999, vol. 125, pp. 1117-1120 (American Medical Assn.; Chicago, Illinois).

A.G. Chiu et al., "Surgical Management of Chronic Rhinosinusitis and Nasal Polyposis: A Review of the Evidence," Current Allergy and Asthma Reports, 2004, vol. 4, pp. 486-489 (Current Science Inc.; Philadelphia, Pennsylvania).

R.A. Chole et al., "Evidence for Microbial Biofilms in Cholesteatomas," Arch. Otolaryngol.—Head and Neck Surg., 2002, vol. 128, pp. 1129-1133 (American Medical Assn.; Chicago, Illinois).

J.W. Costerton et al., "Bacterial Biofilms: A Common Cause of Persistent Infections," Science, 1999, vol. 284, pp. 1318-1322 (Am. Assn. for the Advancement of Science; Washington, D.C.).

J. Cryer et al., "Evidence of Bacterial Biofilms in Human Chronic Sinusitis," ORL, 2004, vol. 66, pp. 155-158 (S. Karger AG; Basel, Switzerland).

M. Desrosiers, "Refractory Chronic Rhinosinusitis Pathophysiology and Management of Chronic Rhinosinusitis Persisting After Endoscopic Sinus Surgery," Current Allergy and Asthma Reports, 2004, vol. 4, pp. 200-207 (Current Science Inc.; Philadelphia, Pennsylvania).

J.R. Dingman et al., "Correlation between Presence of Viable Bacteria and Presence of Endotoxin in Middle-Ear Effusions," J. Clin. Microbiol., 1998, vol. 36, No. 11, 3417-19 (Am. Soc. For Microbiology; Washington, D.C.).

R.M. Donlan, "Biofilms: Microbial Life on Surfaces," Emerging Infectious Diseases, 2002, vol. 8, No. 9, pp. 881-890 (Center for Disease Control; Atlanta, Georgia).

G.D. Ehrlich et al., "Mucosal Biofilm Formation on Middle-Ear Mucosa in the Chinchilla Model of Otitis Media," JAMA, 2002, vol. 287, No. 13, 1710-15 (American Medical Assn.; Chicago, Illinois).

N. Fergie et al., "Is otitis media with effusion a biofilm infection?", Clin. Otolaryngology, 2004, vol. 29, pp. 38-46 (Blackwell Publishing Ltd.; Oxford, UK).

B.J. Ferguson et al., "Demonstration of Biofilm in Human Bacterial Chronic Rhinosinusitis," Am. J. Rhinology, 2005, vol. 19, No. 5, pp. 452-457, (OceanSide Publications, Inc.; Providence, Rhode Island).

F. Götz, "*Staphylococcus* and biofilms," Molecular Microbiology, 2002, vol. 43(6), pp. 1367-1378 (Blackwell Science Ltd.; Oxford, UK).

L. Hall-Stoodley et al., "Direct Detection of Bacterial Biofilms on the Middle-Ear Mucosa of Children With Chronic Otitis Media," JAMA, 2006, vol. 296, No. 2, pp. 202-211 (American Medical Assn.; Chicago, Illinois).

(56) References Cited

OTHER PUBLICATIONS

K.K. Jefferson et al., "Use of Confocal Microscopy to Analyze the Rate of Vancomycin Penetration through *Staphylococcus aureus* Biofilms," Antimicrobial Agents and Chemotherapy, 2005, vol. 49, No. 6, pp. 2467-2473 (Am. Soc. for Microbiology; Washington, D.C.).
F. Lavigne et al., "Selective Irrigation of the Sinuses in the Management of Chronic Rhinosinusitis Refractory to Medical Therapy: A Promising Start," J. Otolaryngology, 2004, vol. 33, No. 1, pp. 10-16 (B.C. Decker Inc.; Hamilton, Ontario, Canada).
J.E. Cho Lieu et al., "Methodologic Assessment of Studies on Endoscopic Sinus Surgery," Arch. Otolaryngol—Head and Neck Surg., 2003, vol. 129, pp. 1230-1235 (American Medical Assn.; Chicago, Illinois).
A. Luong et al., "Sinus Surgery: Indications and Techniques," Clin. Reviews in Allergy & Immunology, 2006, vol. 30, No. 3, pp. 217-222 (Humana Press Inc.; New York, NY).
E.O. Meltzer et al., "Rhinosinusitis: Establishing definitions for clinical research and patient care," J. Allergy Clin. Immunol., 2004, vol. 114, No. 6, pp. S155-S212 (Amer. Acad. of Allergy, Asthma, and Immunology; Milwaukee, Wisconsin).
D.P. Morris et al., "Biofilm: Why the Sudden Interest?", J. Otolaryngology, 2005, vol. 34, supp. 2, pp. S56-S59 (B.C. Decker Inc.; Hamilton, Ontario, Canada).
D.M. Nadel et al., "Endoscopically Guided Cultures in Chronic Sinusitis," Am. J. Rhinology, 1998, vol. 12, No. 4, pp. 233-241 (OceanSide Publications, Inc.; Providence, Rhode Island).
J.N. Palmer, "Bacterial Biofilms: Do They Play a Role in Chronic Sinusitis?", Otolaryng Clin. N. Am., 2005, vol. 38, pp. 1193-1201, (Elsevier Inc.; Maryland Hts., Missouri).
J.R. Perloff et al., "Evidence of Bacterial Biofilms on Frontal Recess Stents in Patients with Chronic Rhinosinusitis," Am. J. of Rhinology, 2004, vol. 18, No. 6, pp. 377-380, (OceanSide Publications, Inc.; Providence, Rhode Island).
J.R. Perloff et al., "Evidence of Bacterial Biofilms in a Rabbit Model of Sinusitis," Am. J. Rhinology, 2005, vol. 19, No. 1, pp. 1-6 (OceanSide Publications, Inc.; Providence, Rhode Island).
J.C. Post, "Direct Evidence of Bacterial Biofilms in Otitis Media," Laryngoscope, 2001, vol. 111, pp. 2083-2094, (The Amer. Laryngological, Rhinological and Otological Society, Inc.; Omaha, Nebraska).
J.C. Post et al., "The role of biofilms in otolaryngologic infections," Current Opinion in Otolaryngology & Head and Neck Surgery, 2004, vol. 12, pp. 185-190 (Lippincott Williams & Wilkins; Baltimore, Maryland).
C. Potera, "Forging a Link Between Biofilms and Disease," Science, 1999, vol. 283, No. 5409, pp. 1837-1839 (Am. Assn. for the Advancement of Science; Washington, D.C.).
H.H. Ramadan et al., "Chronic rhinosinusitis and biofilms," Otolaryngol. Head and Neck Surgery, 2005, vol. 132, No. 3, pp. 414-417 (Amer. Acad. of Otolaryngology—Head and Neck Surgery Foundation, Inc.; Alexandria, Virginia).
M.G. Rayner et al., "Evidence of Bacterial Metabolic Activity in Culture-Negative Otitis Media with Effusion," JAMA, 1998, vol. 279, No. 4, pp. 296-299 (Amer. Med. Assn.; Chicago, Illinois).

J.M. Rosiak et al., "Radiation Formation of Hydrogels for Biomedical Purposes, Some Remarks and Comments," Radiat. Phys. Chem., 1995, vol. 46, No. 2, pp. 161-168 (Elsevier Science Ltd.; London, UK).
J.A. Sanclement et al., "Bacterial Biofilms in Surgical Specimens of Patients with Chronic Rhinosinusitis," Laryngoscope, 2005, vol. 115, pp. 578-582 (The American Laryngological, Rhinological and Otological Society, Inc.; Omaha, Nebraska).
A.R. Sanderson et al., "Bacterial Biofilms on the Sinus Mucosa of Human Subjects With Chronic Rhinosinusitis," Laryngoscope, 2006, vol. 116, pp. 1121-1126 (The American Laryngological, Rhinological and Otological Society, Inc.; Omaha, Nebraska).
T.L. Smith et al., "Evidence Supporting Endoscopic Sinus Surgery in the Management of Adult Chronic Rhinosinusits: A Systematic Review," Am. J. Rhinology, 2005, vol. 19, No. 6, pp. 537-543 (OceanSide Publications, Inc.; Providence, Rhode Island).
S. Stepanović et al., "A Modified microtiter-plate test for quantification of staphylococcal biofilm formation," J. Microbiological Methods, 2000, vol. 40, pp. 175-179 (Elsevier Science B.V.; Amsterdam, Netherlands).
E.L.G.M. Tonnaer et al., "Advances in Understanding the Pathogenesis of Pneumococcal Otitis Media," Pediatr. Infect. Dis. J., 2006, vol. 25, No. 6, pp. 546-552 (Lippincott Williams & Wilkins; Baltimore, Maryland).
Examination report, mailed Jul. 24, 2013, in EP 09819706.4—4 pp.
M.C. Walters III et al., "Contributions of Antibiotic Penetration, Oxygen Limitation, and Low Metabolic Activity to Tolerance of *Pseudomonas aeruginosa* Biofilms to Ciprofloxacin and Tobramycin," Antimicrob. Agents Chemother., 2003, vol. 47, No. 1, pp. 317-323 (Amer. Soc. for Microbiology; Washington, D.C.).
I.J. Witterick et al., "Surgical management of chronic rhinosinusitis," Immunol. Allergy Clin. N. Am., 2004, vol. 24, pp. 119-134, (Elsevier Inc.; Maryland Heights, Missouri).
P. Wormald et al., "A Sheep Model for the Study of Biofilms in Rhinosinusitis," paper from 2006 Annual Meeting of the American Rhinologic Society, held in Toronto, Ontario, Canada (Sep. 2006).
E.D. Wright et al., "Infections Adult Rhinosinusitis: Etiology, Diagnosis, and Management Principles," J. Otolaryngology, 2005, vol. 34, pp. S7-S13 (Supplement 1).
J.C. Carman et al., "Treatment of Biofilm Infections on Implants with Low-frequency Ultrasound and Antibiotics," Am. J. Infect. Control, 2005, 33(2), pp. 78-82 (Elsevier Inc.; Philadelphia, Pennasylvania).
M. Simoes et al., "Action of a cationic surfactant on the activity and removal of bacterial biofilms formed under different flow regimes," Water Research, 39 (2005), pp. 478-486 (Elsevier Ltd.; London, UK).
R.A. Neihof et al., "Biocidal Properties of Anti-Icing Additives for Aircraft Fuels," Appl. Environ. Microbiol., 1978, 35 (4), pp. 698-703 (Am. Socy. for Microbiology; Washington, DC).
Official action dated Jul. 17, 2012 in commonly assigned U.S. Appl. No. 12/573,340.
Official action dated Nov. 23, 2011 in commonly assigned U.S. Appl. No. 12/573,340.
Official action dated Feb. 11, 2013 in commonly assigned U.S. Appl. No. 13/468,767.
Extended Search Report and Search Opinion in EP appl. No. 09819706.4, Sep. 10, 2012.
International Search Report and Written Opinion of the ISR in counterpart int'l appl. No. PCT/US2012/037320, Nov. 29, 2012.

* cited by examiner

ANTIMICROBIAL COMPOSITION AND METHODS FOR USING SAME

CROSS-REFERENCE TO RELATED APPLICATION

This application is a continuation of U.S. patent application Ser. No. 12/573,340 filed 5 Oct. 2009, now abandoned, which claimed the benefit of U.S. provisional application no. 61/103,214 filed 6 Oct. 2008, the entire disclosures of which are incorporated herein by reference.

BACKGROUND INFORMATION

Bacteria is found virtually everywhere and is responsible for a significant amount of disease and infection. Ridding surfaces of bacteria is desirable to reduce human exposure. Bacteria in normal environments have developed self preservation mechanisms and are therefore extremely difficult to remove and/or eradicate.

Bacteria can be found in both planktonic and biofilm forms. In the biofilm form, they interact with surfaces and form surface colonies which adhere to a surface and continue to grow. The bacteria produce exopolysaccharide (EPS) and/or extracellularpoly-saccharide (ECPS) macromolecules that keep them attached to the surface and form a protective film that is effective against many forms of attack. Protection most likely can be attributed to the small diameter of the flow channels in the matrix, which restricts the size of molecules that can transport to the underlying bacteria, and consumption of biocides through interactions with portions of the EPS/ECPS macromolecular matrix.

Additionally, the bacteria in biofilm form are down-regulated (sessile) and not actively dividing. This makes them resistant to attack by a large group of antibiotics and antimicrobials, which attack the bacteria during the active parts of their lifecycle, e.g., cell division.

Due to the protection afforded by the macromolecular matrix and their down-regulated state, bacteria in a biofilm are very difficult to treat. The types of biocides and antimicrobials that are effective in treating bacteria in this form are strongly acidic, oxidizing, and toxic, often involving halogen atoms, oxygen atoms, or both. Common examples include concentrated bleach, strong mineral acids (e.g., HCl) and hydrogen peroxide. Commonly, large dosages of such chemicals are allowed to contact the biofilm for extended amounts of time (up to 24 hours in some circumstances), which makes them impractical for many applications.

Recent developments have involved formulations intended for use against compromised animal/human tissue which, accordingly, are intentionally gentle so as to prevent damage or irritation to compromised tissue. These formulations solvate the biofilm matrix so that still-living bacteria can be rinsed or otherwise removed from infected tissue. The concentrations of active ingredients in these formulations are too low to effectively kill the bacteria in the biofilm, and are thus ill suited for surface disinfection.

A solution that can disrupt the macromolecular matrix, or bypass and/or disable the defenses inherent in these matrices, allowing lethal doses of the antimicrobial ingredients in the solution to access and kill the bacteria in their biofilm and sessile states, remains desirable. Such a solution that is not particularly acidic or caustic (i.e., about $3 \leq pH \leq 9$) and has little to no toxicity would be particularly advantageous.

SUMMARY OF THE INVENTION

Provided herein is an aqueous composition adapted to kill bacteria in both planktonic and biofilm states. In addition to being lethal toward a wide spectrum of gram positive and gram negative bacteria, the composition also exhibits lethality toward other microbes such as viruses, fungi, molds, yeasts, and bacterial spores.

Broadly, the aqueous composition includes a significant amount of one or more surfactants and large amounts of osmotically active solutes. The pH of the composition preferably is moderately low (about $4 \leq pH \leq 6$), although higher concentrations of acidic components can be employed. At least some of the osmotically active solutes include the dissociation product(s) of one or more acids that are effective at interrupting or breaking ionic crosslinks in the macromolecular matrix of the biofilm, which facilitates passage of the solutes and surfactant through the matrix to the bacteria entrained therein and/or protected thereby.

The antimicrobial composition, which is adapted for use against bacteria in a biofilm that includes a macromolecular matrix, can consist essentially of water, dissociation product(s) of one or more organic acids, and at least 1% by weight of one or more surfactants (based on the total weight of the composition). The composition can have an osmolarity of at least 3 Osm/L and a pH of no more than 6.5.

In certain embodiments of the foregoing, the acid(s) can include or consist of one or more organic polyacids.

In at least some embodiments, a portion of the osmotically active solutes result from dissociation of one or more alkali metal salts of the one or more polyacids, the use of which can provide a buffered composition, i.e., a composition which resists significant changes in pH when, for example, some of the hydronium ions are consumed in the crosslink interruption just described.

In at least some embodiments, the composition includes no biocidal additives; in other words, the ingredients just described alone are sufficient to provide significant biocidal activity. Additionally or alternatively, the composition can contain no active ingredients other than acid(s) and surfactant(s).

Without wishing to be bound by theory, the combination of high tonicity (high osmolar concentration) and large amounts of surfactant is believed to induce bacterial membrane leakage, leading to cell lysis. While the ingredients used to prepare such compositions typically are ineffective as bactericides when used at concentrations commonly employed in commercial products, an appropriately formulated composition has been found to be very effective at breaking down or bypassing and disabling biofilm defenses, thereby allowing the composition to access and kill the bacteria, even when it is in a sessile state.

The aqueous composition is lethal toward planktonic and bacterial cells with high efficacy. Advantageously, in many embodiments, it is non-toxic or, at worst, has low toxicity.

Also provided are methods of making and using the foregoing composition. In at least one such method, application of a composition of the type described above to a biofilm can provide at least a 3 log reduction in the number of live bacteria after a residence time of 5 minutes.

To assist in understanding the following description of various embodiments, certain definitions are provided immediately below. These are intended to apply throughout unless the surrounding text explicitly indicates a contrary intention:

"microbe" means any type of microorganism including, but not limited to, bacteria, viruses, fungi, viroids, prions, and the like;

"antimicrobial agent" means a substance having the ability to cause greater than a 90% (1 log) reduction, preferably at least a 99% (2 log) reduction in the number of one or more of microbes including, but not limited to, bacteria selected from *Staphylococcus aureus* and *Pseudomonas aeruginosa*;

"active antimicrobial agent" means an antimicrobial agent that is effective only or primarily during the active parts of the lifecycle, e.g., cell division, of a microbe;

"biofilm" means a community of microbes, particularly bacteria and fungi, attached to a surface with the community members being contained in and/or protected by a self-generated macromolecular matrix;

"residence time" means the amount of time that an antimicrobial agent is allowed to contact a bacterial biofilm;

"entrenched biofilm" is a biofilm that has reached a steady state mass after a growth period of two or more days;

"buffer" means a compound or mixture of compounds having an ability to maintain the pH of a solution to which it is added within relatively narrow limits;

"buffer precursor" means a compound that, when added to a mixture containing an acid, results in a buffer;

"polyacid" means a compound having at least two carboxyl groups and specifically includes dicarboxylic acids, tricarboxylic acids, etc.;

"biocompatible" means presenting no significant, long-term deleterious effects on or in a mammalian species;

"biodegradation" means transformation, via enzymatic, chemical or physical in vivo processes, of a chemical into smaller chemical species;

"biosorption" means absorption of a material into the body of a mammalian species;

"soil load" means a solution of one or more organic and/or inorganic substances added to the suspension of a test organism to simulate the presence of body secretions, excretions, and the like; and "inoculum" means a solution containing bacteria, growth solution (e.g., tryptic soy broth) and protein soil load.

Hereinthroughout, pH values are those which can be obtained from any of a variety of potentiometric techniques employing a properly calibrated electrode.

The relevant portion(s) of any specifically referenced patent and/or published patent application is/are incorporated herein by reference.

DETAILED DESCRIPTION

A composition according to the present invention can result, after no more than 10 minutes residence time, in at least 6 log (99.9999%) reductions in the number of bacteria in an entrenched biofilm. Embodiments of the composition which are non-toxic if ingested can result, after no more than 10 minutes residence time, in at least 4 log (99.99%) reductions in the number of bacteria in an entrenched biofilm. The foregoing compare to commercially available bactericides, where non-toxic versions show less than a 1 log (90%) reduction and toxic versions show 1 to 2 log (90-99%) reductions, with the latter exhibiting a much higher level of toxicity than any embodiment of the presently provided composition.

The composition can contain as few as three ingredients: water, the dissociation product(s) of at least one acid, and at least one surfactant, each of which generally is considered to be biocompatible. The dissociation product(s) of one or more alkali metal salts of organic acids can be included in some embodiments. Certain embodiments of the composition employ no active biocides.

Essentially any source of water can be used, although those that are relatively free of bacteria without advance treatment are preferred. The water need not be distilled, deionized, etc., although such treatments certainly are not excluded. To enhance solubility of one or more of the other components of the composition, the water can be heated.

The composition has a pH less than 7. Without wishing to be bound by theory, acidic protons (i.e., hydronium ions) are believed to be involved in breaking ionic crosslinks in the macromolecular matrix of a biofilm.

Increases in the concentration of hydronium ions, i.e., reductions in pH, generally correspond with enhanced efficacy of the composition. This effect may not be linear, i.e., the enhancement in efficacy may be asymptotic past a certain hydronium ion concentration. As long as the pH of the composition is greater than ~3, the composition generally will be biocompatible; specifically, external exposure will result in no long-term negative dermal effects and ingestion can result biodegradation and/or biosorption, particularly if diluted with water soon after ingestion. If the pH is greater than ~4, accidental inhalation or exposure to an aerosolized version of the composition should not result in laryngospasms or other throat-related damage. However, even those embodiments of the composition having a pH below ~4 are believed to be significantly less toxic than presently available commercial products.

The pH of the composition is less than 7.0, generally less than 6.6, less than 6.4, less than 6.2, less than 6.0, less than 5.8, less than 5.6, less than 5.4, less than 5.2, less than 5.0, less than 4.8, less than 4.6, less than 4.4, less than 4.2, less than 4.0, less than 3.8, less than 3.6, less than 3.6, less than 3.4, less than 3.2, or even less than 3.0; in terms of ranges, the pH of the composition can be from ~2 to ~6.7, from ~2.5 to ~6.5, from ~2.7 to ~6.3, from ~3 to ~6, from ~3.3 to ~5.7, or from ~3.5 to ~5.5.

Acidity is achieved by adding to water (or vice versa) one or more acids, specifically strong (mineral) acids such as HCl, $H_2SO_4$, $H_3PO_4$, $HNO_3$, $H_3BO_3$, and the like or, preferably, organic acids, particularly organic polyacids. Examples of organic acids include monoprotic acids such as formic acid, acetic acid and substituted variants (e.g., hydroxy-acetic acid, chloroacetic acid, dichloroacetic acid, phenylacetic acid, and the like), propanoic acid and substituted variants (e.g., lactic acid, pyruvic acid, and the like), any of a variety of benzoic acids (e.g., mandelic acid, chloromandelic acid, salicylic acid, and the like), glucuronic acid, and the like; diprotic acids such as oxalic acid and substituted variants (e.g., oxamic acid), butanedioic acid and substituted variants (e.g., malic acid, aspartic acid, tartaric acid, citramalic acid, and the like), pentanedioic acid and substituted variants (e.g., glutamic acid, 2-ketoglutaric acid, and the like), hexanedioic acid and substituted variants (e.g., mucic acid), butenedioic acid (both cis and trans isomers), iminodiacetic acid, phthalic acid, and the like; triprotic acids such as citric acid, 2-methylpropane-1,2,3-tricarboxylic acid, benzenetricarboxylic acid, nitrilotriacetic acid, and the like; tetraprotic acids such as prehnitic acid, pyromellitic acid, and the like; and even higher degree acids (e.g., penta-, hexa-, heptaprotic, etc.). Where a tri-, tetra-, or higher acid is used, one or more of the carboxyl protons can be replaced by cationic atoms or groups (e.g., alkali metal ions), which can be the same or different.

In certain embodiments, preference can be given to those organic acids which are, or can be made to be, highly soluble in water; acids that include groups that enhance solubility in water (e.g., hydroxyl groups), examples of which include tartaric acid, citric acid, and citramalic acid, can be preferred in some circumstances. In these and/or other embodiments, preference can be given to those organic acids which are biocompatible; many of the organic acids listed above are used in preparing or treating food products, personal care products, and the like. Alternatively or additionally, preference can be given to those organic acids which can act to chelate the metallic cations ionic involved in crosslinking the macromolecular matrix of the biofilm.

The surfactant component can be added to water before, after or at the same time as the acid(s).

Essentially any material having surface active properties in water can be employed, although those that bear some type of ionic charge are expected to have enhanced antimicrobial efficacy because such charges, when brought into contact with a bacteria, are believed to lead to more effective cell membrane disruption and, ultimately, to cell leakage and lysis. This type of antimicrobial process can kill even sessile bacteria because it does not involve or entail disruption of a cellular process.

Potentially useful anionic surfactants include, but are not limited to, sodium chenodeoxycholate, N-lauroylsarcosine sodium salt, lithium dodecyl sulfate, 1-octane-sulfonic acid sodium salt, sodium cholate hydrate, sodium deoxycholate, sodium dodecyl sulfate, sodium glycodeoxycholate, sodium lauryl sulfate, and the alkyl phosphates set forth in U.S. Pat. No. 6,610,314. Potentially useful cationic surfactants include, but are not limited to, hexadecylpyridinium chloride monohydrate and hexadecyltrimethylammonium bromide, with the latter being a preferred material. Potentially useful nonionic surfactants include, but are not limited to, polyoxyethyleneglycol dodecyl ether, N-decanoyl-N-methyl-glucamine, digitonin, n-dodecyl B-D-maltoside, octyl B-D-glucopyranoside, octylphenol ethoxylate, polyoxyethylene (8) isooctyl phenyl ether, polyoxyethylene sorbitan mono-laurate, and polyoxyethylene (20) sorbitan monooleate. Useful zwitterionic surfactants include but are not limited to 3-[(3-cholamidopropyl)dimethylammonio]-1-propane sulfonate, 3-(decyldimethylammonio)propanesulfonate inner salt, and N-dodecyl-N,N-dimethyl-3-ammonio-1-propanesulfonate. For other potentially useful materials, the interested reader is directed to any of a variety of other sources including, for example, U.S. Pat. Nos. 4,107,328 and 6,953,772 as well as U.S. Pat. Publ. No. 2007/0264310.

The composition contains a sufficient amount (expressed in terms of weight/moles or concentration) of surfactant to interrupt or rupture bacterial cell walls. This amount can vary widely based on a variety of factors including, for example, the age of the biofilm (particularly whether it is entrenched, a factor which relates to the type of proteins and mass of the macromolecular matrix), size of the biofilm, amount of surface soiling, the species of bacteria, whether more than one type of bacteria is present, the solubility of the surfactant(s), and the like. The amount of surfactant generally constitutes greater than ~0.2%, typically at least ~0.5%, more typically at least ~0.7%, often at least ~0.9%, and preferably at least 1% of the composition (with all being weight percentages based on the total weight of the composition), with the upper limit being defined by the solubility limits of the particular surfactant(s) chosen. Some surfactants can permit extremely high loading levels, e.g., at least 5%, at least 10%, at least 12%, at least 15%, at least 17%, at least 20%, or even on the order of ~25% or more (with all being weight percentages based on the total weight of the composition). Any of the foregoing minimum amounts can be combined with any of the foregoing maximum amounts to provide an exemplary range of potential amounts of surfactant.

In certain embodiments, the surfactant(s) can be the only antimicrobial agents in the composition, specifically, the composition can be free of active antimicrobial agents.

The lethality of the surfactant component(s) is increased and/or enhanced when the composition has at least moderate effective solute concentrations (tonicity). (In biological applications, a 0.9% (by wt.) saline solution, which is ~0.3 Osm/L, typically is considered to be have moderate tonicity, while a 3% (by wt.) saline solution, which is ~0.9 Osm/L, generally is considered to be hypertonic.) Without wishing to be bound by theory, compositions having higher tonicities may exert higher osmotic pressure to the bacterial cell wall, which increases its susceptibility to interruption by surfactant.

The osmolarity of the composition generally increases in proportion with the amount of acid(s) employed, with the osmolarity maximum for a given composition primarily being a function of the solubility limits of the specific acid, i.e., the point at which the acid(s) begin to no longer be soluble. An obvious corollary to increased levels of acid(s) in the composition is higher concentrations of hydronium ions, i.e., low pH values. As noted previously, some end-use applications can call for a composition with only a moderately low pH. To increase the osmolarity of a composition without depressing its pH past a desired target, one or more types of other water soluble compounds can be included. Such compounds, upon dissociation, increase the effective amount of solutes in the composition without greatly impacting the molar concentration of hydronium ions while, simultaneously, providing a buffer system in the composition.

One approach to achieve increased tonicity of the composition is by adding large amounts of ionic compounds (salts); see, e.g., U.S. Pat. No. 7,090,882. Where one or more organic acids are used in the composition, a preferred approach to increasing tonicity involves inclusion of salt(s) of one or more the acid(s) or the salt(s) of one or more other organic acids. For example, where the composition includes x moles of an acid, a many fold excess (e.g., 3x-10x, preferably at least 5x or even at least 8x) of one or more salts of that acid also can be included. The identity of the countercation portion of the salt is not believed to be particularly critical, with common examples including ammonium ions and alkali metals. Where a polyacid is used, all or fewer than all of the carboxyl H atoms can be replaced with cationic atoms or groups, which can be the same or different. For example, mono-, di- and trisodium citrate all constitute potentially useful buffer precursors. However, because trisodium citrate has three available basic sites, it has a theoretical buffering capacity up to 50% greater than that of disodium citrate (which has two such sites) and up to 200% greater than that of sodium citrate (which has only one such site).

Regardless of how achieved, the tonicity of the composition is at least moderately high, with an osmolarity of at least about 1 Osm/L being preferred for most applications. Depending on particular end-use application, the composition can have any of the following concentrations: at least ~1.5 Osm/L, at least ~1.75 Osm/L, at least ~2.0 Osm/L, at least ~2.25 Osm/L, at least ~2.5 Osm/L, at least ~2.75 Osm/L, at least ~3.0 Osm/L, at least ~3.25 Osm/L, at least ~3.5 Osm/L, at least ~3.75 Osm/L, at least ~4.0 Osm/L, and even at least ~4.25 Osm/L. Certain embodiments of the composition can exhibit solute concentrations of 1 to 5 Osm/L, 1.2 to 4.5 Osm/L, 1.4 to 4.4 Osm/L, 1.6 to 4.3 Osm/L, 1.8 to 4.2 Osm/L, 1.9 to 4.1 Osm/L, and 2 to 4 Osm/L; other potentially useful ranges include 3-5 Osm/L, 2.5-4.5 Osm/L, 3-4.5 Osm/L, 3.5-5 Osm/L, 3.25-4.5 Osm/L, and the like.

While the characteristics of the acid(s), surfactant(s) and optional (non-acid) water soluble compounds have been described in isolation, combinations of individual values or ranges for one component can be provided in conjunction with values or ranges for one or both of the other components. For example, a biocompatible composition (i.e., minimal toxicity) can entail a pH maintained above ~4, an effective solute concentration of at least ~0.10 Osm/L, and large amounts of one or more surfactant(s). Increasing the pH to ~6 or higher can increase biocompatibility of the composition but, simultaneously, decrease its efficacy in killing microbes; conversely, decreasing the pH below ~4 and/or increasing the osmolarity of the composition can increase its antimicrobial capacity while, simultaneously, reducing its biocompatibility. Generally, no particular benefit is seen from reducing the amount of surfactant employed, although too high of an amount can present toxicity concerns in some circumstances.

The composition can be prepared in a number of ways. Description of an exemplary method follows.

Acid (e.g., anhydrous citric acid), optional buffer precursor (e.g., a citric acid salt such as sodium citrate dihydrate), and sufficient water to constitute ~80% of the calculated desired volume. This solution can be stirred and/or heated to promote solution of the acid and optional buffer precursor. The desired amount of surfactant(s) then can be added before additional water is added to bring the composition close to the calculated volume. Once stirring, if used, is complete, sufficient water is added so as to bring the composition to the calculated value. Advantageously, no special conditions or containers are needed to store the composition for an extended time, although refrigeration can be used if desired.

A variety of additives and adjuvants can be included to make a composition more amenable for use in a particular end-use application with negatively affecting its efficacy in a substantial manner. Examples include, but are not limited to, emollients, fungicides, fragrances, pigments, dyes, defoamers, foaming agents, flavors, abrasives, bleaching agents, preservatives (e.g., antioxidants) and the like.

The composition does not require inclusion of an active antimicrobial agent for efficacy, but such materials can be included in certain embodiments. For example, one or more of bleach, any of a variety of phenols, aldehydes, quaternary ammonium compounds, etc., can be added.

The composition conveniently can be provided as a solution, although other forms might be desirable for certain end-use applications. Accordingly, the composition can be provided as a soluble powder (for subsequent dilution, an option which can reduce transportation costs), a slurry, or a thicker form such as a gel or paste (which might be particularly useful for providing increased residence times). For the latter, the composition can include additional ingredients such as a coalescent (e.g., polyvinylpyrrolidone).

Embodiments of the composition can provide very large reductions in the number of bacteria, even with extremely short residence times. For example, a composition having high concentrations of surfactant (e.g., 1.5-2.5% by wt.) and total solutes (e.g., 3-4 Osm/L) can provide a 2, 3 or 4 log (99.99%) reduction in the number of bacteria in an entrenched biofilm with a 3, 4, 5, 7, 8, 9, or 10 minute residence time and a 3, 4, 5, or 6 log (99.9999%) reduction in the number of planktonic bacteria with a mere 30-second residence time.

Quantitative Carrier Testing (ASTM E2197) is designed to determine the contact time necessary to eradicate from a surface (e.g., countertops, sinks, bathroom fixtures, and the like) bacteria in a soil-loaded inoculum. In this test, bacteria combined with a soil loading and a 10 µL inoculum is placed on a stainless steel carrier disk. After the inoculate is allowed to dry completely, 50 µL of antimicrobial treatment composition is applied and allowed to stay in place for the desired treatment time, after which dilution with a saline dilution is performed. The following are results achieved from Quantitative Carrier Testing using 5% soil load and a 3 minute residence time (with TDTMAB representing tetradecyltrimethylammonium bromide):

0.021 M caprylyl sulfobetaine, 3.2 Osm/L, 6.5 pH—5.2 log reduction of *pseudomonas*

0.028 M caprylyl sulfobetaine, 3.6 Osm/L, 5.5 pH—3.1 log reduction of staph and 5.9 log reduction of *pseudomonas*

0.041 M TDTMAB, 3.5 Osm/L, 6.5 pH—5.1 log reduction of staph and 7.5 log reduction of *pseudomonas*

0.027 M TDTMAB, 3.5 Osm/L, 6.5 pH—4.9 log reduction of staph and 5.2 log reduction of *pseudomonas*

0.041 M TDTMAB, 1.8 Osm/L, 6.5 pH—3.2 log reduction of staph and 5.2 log reduction of *pseudomonas*

0.027 M TDTMAB, 1.8 Osm/L, 6.5 pH—3.2 log reduction of staph and 4.7 log reduction of *pseudomonas*

0.014 M TDTMAB, 1.8 Osm/L, 6.5 pH—2.9 log reduction of staph and 4.5 log reduction of *pseudomonas*

Where the third composition was used again at a one-minute residence time, the results were a 5.1 log reduction of staph (i.e., no change, indicating that much of the killing of staph bacteria may occur in the first minute), and a 6.8 log reduction of *pseudomonas*.

An alternative test designed to show efficacy against an entrenched biofilm involves treatment of biofilm-forming bacterial strains grown over several days (typically in an incubator at 37° C. and aerobic conditions) in a drip-flow reactor, designed to model growth in a low shear environment. Bacteria are inoculated (e.g., on glass slides, optionally coated with hydroxyapatite) pre-coated with a sterile medium (e.g., trypticase soy broth). A coated slide then is inoculated with a culture of the biofilm-forming microbe of interest. The reactor is placed in a horizontal position (typically ~2 hours) to promote bacterial attachment to the substrate before being inclined (e.g., to a 10° angle), with sterile medium dripping on the slides (typically at a rate of ~$2.78 \times 10^{-3}$ mL/sec). After a desired number of days of growth, flow of the sterile medium is halted, and the reactor is raised to horizontal. Antimicrobial composition is applied, while a control slide is treated with saline solution. After an amount of time (typically 5-10 minutes), the slides are rinsed with saline solution. Each slide is removed and placed in a sterile container, scraped, vortexed, and sonicated multiple times to harvest bacteria which are then incubated on plates for counting. Efficacy is calculated by subtracting the bacterial count on a treated slide from the bacterial count on a control (non-treated) slide. The following are results achieved from this test using a 5 minute residence time:

0.028 M caprylyl sulfobetaine, 3.5 Osm/L, 6.5 pH—2.8 log reduction of staph and 6.0 log reduction of *pseudomonas*

0.023 M octyl sulfobetaine, 3.5 Osm/L, 6.5 pH—1.4 log reduction of staph and 6.2 log reduction of *pseudomonas*

0.016 M TDTMAB, 0.8 Osm/L, 6.5 pH—3.0 log reduction of staph and 2.2 log reduction of *pseudomonas*

0.041 M TDTMAB, 3.5 Osm/L, 6.5 pH—8.9 log reduction of staph and 6.7 log reduction of *pseudomonas*

The foregoing data includes much of interest including, for example, a potential indication that *pseudomonas*, a gram negative bacteria, is more affected by the osmolarity of the composition than by the type or concentration of surfactant employed, while the opposite might be true for staph.

The foregoing levels of bactericidal activity are greater than for most strong chemical treatments in current use, even though the composition is far less toxic (i.e., more biocompatible) than those treatments. Generally, longer residence times can result in greater reductions in the number of bacteria, although the effect may be asymptotic.

The composition can be employed in a variety of ways. For example, when used to treat a biofilm on a surface (e.g., cutting board, counter, desk, etc.), the composition can be applied directly to the biofilm, optionally followed by physical rubbing or buffing, or the composition can be applied to the rubbing/buffing medium, e.g., cloth. Where a biofilm in an inaccessible area is to be treated, soaking or immersion of the biofilm in an excess of the composition can be performed for a time sufficient to essentially solvate the biofilm, which then can be flushed from the affected area. Regardless of contact method, the surfactant component(s) are believed to kill significant numbers of bacteria without a need for the bacteria to be removed from the biofilm or vice versa.

Due to the abundance of microbial contamination, the composition may find utility in a large number of potential uses including, but not limited to, household applications including non-compromised skin (hand, hair, and body washing), kitchen cleaning (countertop and surface cleaning, cleaning of food preparation utensils, dish washing, produce washing, etc.), bathroom cleaning (countertop and surface cleaning, fixture cleaning, toilet bowl cleaning and shower mildew eradication), and laundry area cleaning (including laundry detergent and diaper sterilization); commercial applications include livestock care (facility and equipment sterilization and dairy teat dip), produce sterilization (an alternative to irradiation, which can be particularly useful against *e-coli, listeria, salmonella*, botulism, etc.), commercial kitchen (countertop and surface cleaning, food preparation utensil cleaning, storage equipment and facilities cleaning, dish washing and produce washing), mass food and beverage processing (processing and storage equipment cleaning, tank sterilization, cleaning of liquid transport lines, etc.), cleaning of water lines (e.g., for drinking water, dental offices, plumbing, and the like), and food and beverage transport (cleaning of tanker units for semi transport, cleaning of tanker cars for railroad transport, and cleaning of pipelines); and non-traditional uses such as denture cleaning, acne treatment, spermicides, laboratory equipment cleaning, laboratory surface cleaning, oil pipeline cleaning, and test article processing for biofilm attachment.

While various embodiments of the present invention have been provided, they are presented by way of example and not limitation. The following claims and their equivalents define the breadth and scope of the inventive methods and compositions, and the same are not not to be limited by or to any of the foregoing exemplary embodiments.

That which is claimed is:

1. An antimicrobial composition useful for cleaning and disinfecting a food contact surface, said composition consisting of
   a) water,
   b) dissociation product of one or more biocompatible organic acids,
   c) dissociation product of a buffer precursor, and
   d) at least about 0.2% by weight cationic surfactant,
   said composition having a pH of less than 4.0 and an effective solute concentration of from 1.8 to 4.2 Osm/L.

2. The antimicrobial composition of claim 1 wherein said composition has an effective solute concentration of from 2 to 4 Osm/L.

3. The antimicrobial composition of claim 2 wherein said composition has an effective solute concentration of at least about 2.25 Osm/L.

4. The antimicrobial composition of claim 1 wherein said composition has an effective solute concentration of at least about 2 Osm/L.

5. The antimicrobial composition of claim 1 wherein said cationic surfactant comprises at least one of hexadecylpyridinium chloride monohydrate, hexadecyltrimethylammonium bromide, and tetradecyltrimethylammonium bromide.

6. The antimicrobial composition of claim 1 wherein said one or more biocompatible organic acids comprises at least one polyacid.

7. The antimicrobial composition of claim 6 wherein said at least one polyacid comprises citric acid.

8. The antimicrobial composition of claim 7 wherein said composition comprises at least one buffer precursor which comprises a sodium salt of citric acid.

9. The antimicrobial composition of claim 6 wherein said at least one polyacid is citric acid.

10. The antimicrobial composition of claim 9 wherein said composition comprises at least one buffer precursor which comprises a sodium salt of citric acid.

11. The antimicrobial composition of claim 6 wherein each of said one or more biocompatible organic acids is a polyacid.

12. The antimicrobial composition of claim 6 wherein said polyacid is citric acid.

13. The antimicrobial composition of claim 12 wherein said composition comprises at least one buffer precursor which comprises a sodium salt of citric acid.

14. The antimicrobial composition of claim 1 wherein said one or more biocompatible organic acids is a polyacid.

15. An antimicrobial composition useful for cleaning and disinfecting a food contact surface, said composition consisting of
   a) water,
   b) dissociation product of one or more biocompatible organic acids that comprise at least one polyacid,
   c) dissociation product of a buffer precursor that comprises a sodium salt of a polyacid, and
   d) at least about 0.2% by weight cationic surfactant,
   said composition having a pH of less than 4.0 and an effective solute concentration of from 1.8 to 4.2 Osm/L.

16. The antimicrobial composition of claim 15 wherein said composition has an effective solute concentration of from 2 to 4 Osm/L.

17. The antimicrobial composition of claim 15 wherein said one or more biocompatible organic acids is citric acid and wherein said buffer precursor is a sodium salt of citric acid.

18. An antimicrobial composition useful for cleaning and disinfecting a food contact surface, said composition consisting of
   a) water,
   b) dissociation product of one or more biocompatible polyacids,
   c) dissociation product of a buffer precursor that is a sodium salt of at least one polyacid, and
   d) at least about 0.2% by weight cationic surfactant,
   said composition having a pH of less than 4.0.

19. The antimicrobial composition of claim 18 wherein said one or more biocompatible polyacids comprises citric acid.

20. The antimicrobial composition of claim 18 wherein said sodium salt of at least one polyacid comprises trisodium citrate.

21. The antimicrobial composition of claim 18 wherein said sodium salt of at least one polyacid is trisodium citrate.

* * * * *